(12) United States Patent
Mitani

(10) Patent No.: US 7,677,886 B2
(45) Date of Patent: Mar. 16, 2010

(54) MAXILLOFACIAL ORTHODONTIC APPLIANCE

(76) Inventor: Yasushi Mitani, 20-13, Kichijoji-honcho 4-chome, Musashino-shi, Tokyo 180-0004 (JP)

( * ) Notice: Subject to any disclaimer, the term of this patent is extended or adjusted under 35 U.S.C. 154(b) by 0 days.

(21) Appl. No.: 12/246,673

(22) Filed: Oct. 7, 2008

(65) Prior Publication Data

US 2009/0098499 A1  Apr. 16, 2009

(30) Foreign Application Priority Data

Oct. 10, 2007 (JP) .............................. 2007-264078

(51) Int. Cl.
*A61C 7/00* (2006.01)
(52) U.S. Cl. .............................................. 433/5; 433/7
(58) Field of Classification Search ...................... 433/5, 433/7, 18, 24
See application file for complete search history.

(56) References Cited

U.S. PATENT DOCUMENTS

| | | | | |
|---|---|---|---|---|
| 2,334,894 A | * | 11/1943 | Atkinson ........................ | 433/5 |
| 4,026,023 A | * | 5/1977 | Fisher ............................ | 433/7 |
| 5,002,485 A | * | 3/1991 | Aagesen ......................... | 433/7 |
| 5,810,583 A | * | 9/1998 | Doyle ............................. | 433/5 |
| 5,829,970 A | * | 11/1998 | Yousefian ....................... | 433/7 |
| 7,074,036 B1 | * | 7/2006 | Keles ............................. | 433/7 |
| 7,121,824 B2 | * | 10/2006 | Keles et al. .................... | 433/5 |

FOREIGN PATENT DOCUMENTS

| | | |
|---|---|---|
| EP | 0919207 | 6/1999 |
| JP | 11-169385 | 6/1999 |
| JP | 2006-42963 | 2/2006 |
| JP | 2006-280689 | 10/2006 |

* cited by examiner

*Primary Examiner*—Ralph A Lewis
(74) *Attorney, Agent, or Firm*—Myers Wolin, LLC

(57) ABSTRACT

A maxillofacial orthotic appliance comprises: a maxilla expander fixed to the maxilla in the mouth of a human and a towed-unit which is connected to the maxilla expander and is towed in an anterior direction from the human. The towed-unit includes: a left wire whose one end is inserted into the left hole of the maxilla expander and the other end is protruding out of the mouth, a right wire whose one end is inserted into the right hole of the maxilla expander and the other end is protruding out of the mouth, a connecting tube provided on the left or right wire and extending in the direction of the distance variation, caused by the maxilla-expander adjusting mechanism, between the left and right contact parts and a connecting wire provided on the other of the left and right wires and inserted into the connecting tube slidably.

9 Claims, 12 Drawing Sheets

MAXILLOFACIAL ORTHODONTIC APPLIANCE

CROSS REFERENCE TO RELATED APPLICATIONS

The present disclosure claims priority to Japanese Patent Application No. 2007-264078 filed on Oct. 10, 2007 (now Japanese Patent No. 4,058,105 issued Dec. 21, 2007), the disclosure of which is expressly incorporated herein by reference in its entireties.

BACKGROUND OF THE INVENTION (1) Field of the Invention

The present invention relates to a maxillofacial orthodontic appliance that can be used preferably for correcting malocclusion.

(2) Description of Related Art

Conventionally, various methods have been used for correcting malocclusion.

In the case of maxillary protrusion (so-called, prominent teeth) caused by malocclusion, it is common to adopt a treatment in which the maxillary dental arch is retracted (moved distally). On the other hand, in a case of mandibular protrusion (so-called, protruding lower lip and jaw), it is common to adopt a treatment in which the mandibular dental arch is retracted (moved distally).

In the following, an explanation will be given on a typical example of a distal movement treatment of teeth, referring to FIG. 7. FIG. 7(A) to FIG. 7(C) are all diagrams illustrating teeth of a maxilla from within an oral cavity.

When a crowding of anterior teeth $T_1$, $T_2$, $T_3$ is seen, as shown in FIG. 7(A), it is common to take a treatment for correcting the dental arch in which spaces $G_4$, $G_4$ are secured by extracting the fourth teeth (first premolars) $T_4$, $T_4$ (see FIG. 7(B)) and then the third teeth (canines) $T_3$, $T_3$, the second teeth (lateral incisors) $T_2$, $T_2$ and the first teeth (central incisors) $T_1$, $T_1$ are moved distally.

Incidentally, though a distal movement treatment of maxillary teeth was explained above, a distal movement treatment of mandibular teeth is almost the same as the method described above referring to FIG. 7. However, in a distal movement treatment of mandibular teeth, the fifth teeth of the mandible (mandibular second premolars) may be extracted.

In such a method, the distance by which the dental arch can be moved is small and thus a severe case of malocclusion can not be treated. Therefore, according to the circumstances, a surgical treatment including amputation of bones may be carried out.

The above-described method of orthodontic treatment is generally known. Moreover, appliances used for such an orthodontic treatment are also widely known. An example of such kind of appliance is disclosed in Patent Document 1 below.

However, even with an orthodontic treatment by means of a distal movement, such as described above, or a surgical treatment, malocclusion relapses after several years have passed.

Most of the researchers have been conventionally supported the hypothesis that such relapses occur for the reason that malocclusion is hereditary.

Specifically speaking, by such an inheritance-based theory, an explanation that a genetic cause will induce relapse of irregular teeth and malocclusion even with a distal movement treatment or a surgical treatment of teeth will be given.

[Patent Document 1] Japanese Patent Laid-Open Publication (Kokai) No. 2006-42963

SUMMARY OF THE INVENTION

However, the present inventor considers that the cause of malocclusion is not an inheritance but an improper forward development of the maxilla and a malocclusion is induced by such irregular teeth. In other words, the present inventor considers that it is actually difficult to correct malocclusion fundamentally, if the maxilla is not developed forward properly, even with any orthodontic or surgical treatment.

This point will be explained in more detail.

FIG. 8 shows an example of a treatment method for developing a maxilla forward.

In this method, a maxillary protraction appliance 102 is fixed to the face 101 of a human 100.

This maxillary protraction appliance 102 comprises a head support 104 contacting the forehead 103, a chin support contacting the lower end 106 of the mandible 105, a metal main frame 108 interconnecting the head support 104 and the chin support 107 and extending vertically.

On the main frame 108, an outer hook 109 sticking out in the opposite direction of the face 101 is provided. An elastic 111 is hooked on the outer hook 109. In addition, the outer hook 109 is disposed on the main frame 108 so that it is located in front of the nose 112 when the maxillary protraction appliance 102 is fixed to the face 101.

Furthermore, in this treatment method, an inner hook is provided on the maxilla 113, and the above-mentioned elastic 111 is hooked with this inner hook 114. The inner hook 114 is a component provided in pairs on a maxilla expander (not shown in the drawings) fixed to the maxilla 114 in the oral cavity, and they protrude upward at the left and right outside of the maxillary tooth row 115, respectively.

In this way, the biasing force of the elastic 111 acts so that the distance between the inner hook 114 and the outer hook 109 is shortened. In other words, the inner hook 114 is protracted, as shown in the drawing with the arrow $F_{109}$.

However, in this case, an anticlockwise moment acts on the maxilla 113, as shown in FIG. 8 by the arrow $M_{113}$. It displaces not only PNS (Posterior Nasal Spine) but also the condyle 116, which is the upper end of the mandible 105, downward.

Accordingly, by the method shown in FIG. 8, it is difficult to suppress the symptom of mandibular protrusion. If it can suppress the symptom of mandibular protrusion to some extent, a gap between the anterior teeth of the maxilla 113 and the mandible 105 may be formed (namely, the lips may be unsealed).

In addition, the distance from the lower end of the subnasal point 112 of the face 101 to the lower end 106 of the mandible 105 (namely, LFH (Lower Facial Height)) may be elongated relative to that before the treatment.

Furthermore, a downward displacement of the PNS causes another problem of difficulty in keeping the tongue in contact with the under surface of the maxilla 114 in the oral cavity. An explanation will be given on that, referring to FIG. 9 and FIG. 10.

FIG. 9 is a side sectional view partially illustrating a face 121 of a human 120 whose occlusion is normal. FIG. 10 is a side sectional view partially illustrating a face of a human 140 who suffers from mandibular protrusion.

The soft palate 122 of the human 120 (refer to FIG. 9) whose occlusion is normal is positioned higher than the soft palate 142 of the human 140 (refer to FIG. 10) suffering from mandibular protrusion. Therefore, in the case of the human whose occlusion is normal, shown in FIG. 9, the movable space $S_{120}$ for the tongue (namely, tongue range of motion) (not shown in the drawings) within the oral cavity is secured throughout the oral cavity. In addition, a space in the oral cavity for keeping the tongue in contact with the under surface of the maxilla 123 can be sufficiently remained.

In contrast, the tongue range of motion $S_{140}$ of the human who suffers from mandibular protrusion shown in FIG. 10 is smaller than the tongue range of motion $S_{120}$ of the human whose occlusion is normal. In such a case, the tongue can not reach the under surface of the maxilla 143, and thus a gap $G_{140}$ is created.

In the treatment method shown in FIG. 8, a downward displacement of the PNS promotes the downward displacement of the soft palate 142, as shown in FIG. 10.

In the following, a brief explanation will be given on the relationship between the downward displacement of the soft palate and the onset of mandibular protrusion.

As shown in FIG. 11, a paranasal sinus 152 is formed within the head 151 of a human 150. When air is aspirated from the nose 153, the air filled into the paranasal sinus 152 heighten the atmospheric pressure within the paranasal sinus 152 (namely, it produces a positive pressure). The produced positive pressure within the paranasal sinus 152 presses the soft palate 154 and the hard palate 155 downward and forward. This pressing force is considered to be the acceleration factor for the forward growth of the maxilla 156.

Therefore, for correcting a mandibular protrusion, it is necessary to produce a positive pressure in the paranasal sinus 152, because a proper forward development of the maxilla 156 is necessary for correcting a mandibular protrusion. Then, in order to produce a positive pressure in the paranasal sinus 152, nasal breathing, not mouth breathing, should be taken.

However, as described earlier, in the human 140 of FIG. 10 who suffers from mandibular protrusion, the tongue can not be kept in contact with the under surface of the maxilla 143 in the oral cavity due to the downward displacement of the soft palate 142.

But, it is physiologically very difficult to breathe through the nose with the tongue apart from the under surface of the maxilla 143.

If the tongue can be kept touching the under surface of the maxilla 143, the nasal breathing can be performed smoothly. However, if the tongue can not be kept touching the under surface of the maxilla 143, the breathing is performed through the mouth inevitably.

By the treatment method described above referring to FIG. 8, nasal breathing is after all inhibited and the environment will have difficulty in producing a positive pressure in the paranasal sinus, which fails to accelerate a proper forward development of the maxilla and prevent the occurrence of a mandibular protrusion.

In addition, when a space for keeping the tongue in contact with the under surface of the maxilla 143 can not be secured in the oral cavity, the tongue protrudes from between the teeth 146 of the maxilla 143 and the teeth 145 of the mandible 144. In the result, a forward lingual pressure always acts on the teeth 145 of the mandible 144 from inside the oral cavity (refer to $P_{140}$ in FIG. 10), which further accelerates the symptom of mandibular protrusion.

Though the explanation has been given on the case where mouth breathing, not nasal breathing, accelerates the mandibular protrusion using FIG. 9 to FIG. 11, there is another case where a maxillary protrusion is accelerated. This case will be explained below using FIG. 12, which is a side sectional view partially illustrating the face 161 of a human 160 who suffers from maxillary protrusion.

As shown in FIG. 12, the tongue range of motion $S_{160}$ of the human 160 who suffers from maxillary protrusion is also smaller than the tongue range of motion $S_{120}$ of the human 120 whose occlusion is normal, and the tongue incapable of reaching the under surface of the maxilla 163 creates a gap $G_{160}$. As a result, it is difficult for the human 160 who suffers from maxillary protrusion to keep the tongue contacting the under surface of the maxilla 163, which leads to his mouth breathing inevitably. Moreover, a positive pressure can not be created in the paranasal sinus (not shown in FIG. 12), because the tongue can not push up the soft palate 162.

Therefore, the forward development of the maxilla 163 is inhibited. However, when the maxilla 163 in the course of growth period is inhibited to grow forward, it grows downward.

On the other hand, the mandible 164, of which forward development follows the forward development of the maxilla 163, cannot develop forward, insofar as the forward development of the maxilla 163 is inhibited as described above. Moreover, since the maxilla 163 develops downward, the symptom of maxillary protrusion is further accelerated.

In addition, when a space for keeping the tongue in contact with the under surface of the maxilla 163 can not be secured in the oral cavity, the tongue protrudes from between the teeth 165 of the maxilla 163 and the teeth 166 of the mandible 164. As a result, a forward lingual pressure always acts on the teeth 165 of the mandible 163 from inside the oral cavity (refer to $P_{160}$ in FIG. 12), which further accelerates the symptom of maxillary protrusion.

On the other hand, the distal movement treatment, explained at the beginning, is also a problem because it goes against the direction of the human growth.

In other words, the direction of development of bones of the maxilla and mandible (namely, jaw bones), which occurs naturally accompanying the craniofacial development, is always mesial (namely, forward) and also the direction of teeth eruption is always forward. However, in a distal movement treatment, teeth are forced to be moved distally (namely, backward), as described earlier. Therefore, distal movement treatments go against the direction of intrinsic growth of humans.

The present invention has been made in view of such problems. The purpose of the present invention is to provide a maxillofacial orthodontic appliance that can correct malocclusion by means of promoting a proper forward development of the maxilla.

For achieving the above purpose, the maxillofacial orthodontic appliance of the present invention is characterized in that it comprises: a maxilla expander which is fixed to the maxilla in the mouth of a human and a towed-unit to be towed which is connected to said maxilla expander and towed in an anterior direction from the human, wherein said maxilla expander comprises: a left contact part pushing the left maxillary tooth row of the human from within, a right contact part pushing the right maxillary tooth row of the human from within, an adjusting mechanism connecting said left contact part and said right contact part with the distance between said left contact part and said right contact part being variable, a left hole formed on said left contact part and a right hole formed on said right contact part, and said towed-unit comprises: a left wire whose one end is inserted into said left hole and the other end is protruding out of the mouth, a right wire whose one end is inserted into said right hole and the other end is protruding out of the mouth, a connecting tube provided on one of said left wire and said right wire and extending in the direction of the variation of the distance, caused by said adjusting mechanism, between said left contact part and said right contact part and a connecting wire provided on the other of said left wire and said right wire and inserted into said connecting tube slidably.

In addition, the maxillofacial orthodontic appliance of the present invention is characterized in that it comprises: a left-A tip wire provided in the vicinity of the tip of said left wire and sticking out upward, a right-A tip wire provided in the vicinity of the tip of said right wire and sticking out upward, a left-first-A projection provided on said left-A tip wire and projecting toward the face of the human and a right-first-A projection provided on said right-A tip wire and projecting toward the face of the human, said left-first-A projection being hooked with a left-first elastic body which tows said left wire anteriorly and horizontally, and said right-first-A projection being hooked with a right-first elastic body which tows said right wire anteriorly and horizontally.

In addition, the maxillofacial orthodontic appliance of the present invention is characterized in that said connecting tube opens at both ends, and said connecting wire passes through said connecting tube.

In addition, the maxillofacial orthodontic appliance of the present invention is characterized in that a pair of said connecting tubes are provided on one of said left wire and said right wire, and a pair of said connecting wires are provided on the other of said left wire and said right wire.

In addition, the maxillofacial orthodontic appliance of the present invention is characterized in that a pair of said connecting tubes have the same inner diameters, one of said pair of connecting wires has the first external diameter which is smaller than the inner diameter of said connecting tubes in 0.1 to 0.05 mm, and the other of said pair of connecting wires has the second external diameter which is smaller than the first external diameter.

In addition, the maxillofacial orthodontic appliance of the present invention is characterized in that it comprises: a head support fixed to the head of the human, a chin support fixed to the mandible of the human, a pair of side frames extending in the vertical direction, of which upper end is connected to said head support and lower end is connected to said chin support, a horizontal bar extending from left to right in front of the face of the human at higher position than the mouth of the human and connecting said pair of side frames, a left-B extended bar extending from said horizontal bar in front of and at the left side of the face with its tip being disposed forward of the mouth, a right-B extended bar extending from said horizontal bar in front of and at the right side of the face with its tip being disposed forward of the mouth, a left-first-B projection provided in the vicinity of the tip of said left-B extended bar and hooked with said left-first elastic body and a right-first-B projection provided in the vicinity of the tip of said right-B extended bar and hooked with said right-first elastic body, said left-first elastic body connecting said left-first-A projection and said left-first-B projection, and said right-first elastic body connecting said right-first-A projection and said right-first-B projection.

In addition, the maxillofacial orthodontic appliance of the present invention is characterized in that it comprises: a head support fixed to the head of the human, a chin support fixed to the mandible of the human, a pair of side frames extending in the vertical direction, of which upper end is connected to said head support and lower end is connected to said chin support, a horizontal bar extending from left to right in front of the face of the human at higher position than the mouth of the human and connecting said pair of side frames, a left-B extended bar extended from said horizontal bar in front of and at the left side of the face with its tip being disposed forward of the mouth, a right-B extended bar extended from said horizontal bar in front of and at the right side of the face with its tip being disposed forward of the mouth, a left-first-B projection provided in the vicinity of the tip of said left-B extended bar and hooked with said left-first elastic body and a right-first-B projection provided in the vicinity of the tip of said right-B extended bar and hooked with said right-first elastic body, said left-first elastic body connecting said left-first-A projection and said left-first-B projection, and said right-first elastic body connecting said right-first-A projection and said right-first-B projection.

Therefore, according to the maxillofacial orthodontic appliance of the present invention, a malocclusion can be corrected by means of promoting a proper forward development of the maxilla, regardless of an individual difference in the shape of the oral cavity and a stage of treatment.

Further, in addition to the force pushing the maxilla upward from within the oral cavity, a force pushing it forward from within the oral cavity can also be applied. This enables to promote a proper growth of the maxilla.

Moreover, an easy untying of the connection between the left wire and the right wire can be prevented, even with a considerable change in the width of the maxilla expander or twist of the left wire and the right wire.

Moreover, by inserting a pair of connecting wires into a pair of connecting tubes, the right wire and the left wire can be interconnected surely.

Moreover, the right wire and the left wire can be connected properly, allowing an easy adjusting of the distance between the right wire and the left wire (namely, the width of the towed-unit).

Moreover, the right wire and the left wire can be biased forward appropriately, allowing the width of the towed-unit to be changed.

Moreover, the moment that pushes the maxilla expander fixed in the oral cavity upward can be adjusted so that it does not become excessively large, allowing the width of the towed-unit to be changed. This can prevent the detachment of the maxilla expander from the maxillary oral cavity.

BRIEF DESCRIPTION OF THE DRAWINGS

In FIG. 1, it is fixed to a human.

In FIG. 2, it is fixed to a human.

DESCRIPTION OF THE PREFERRED EMBODIMENTS

Figure 1:
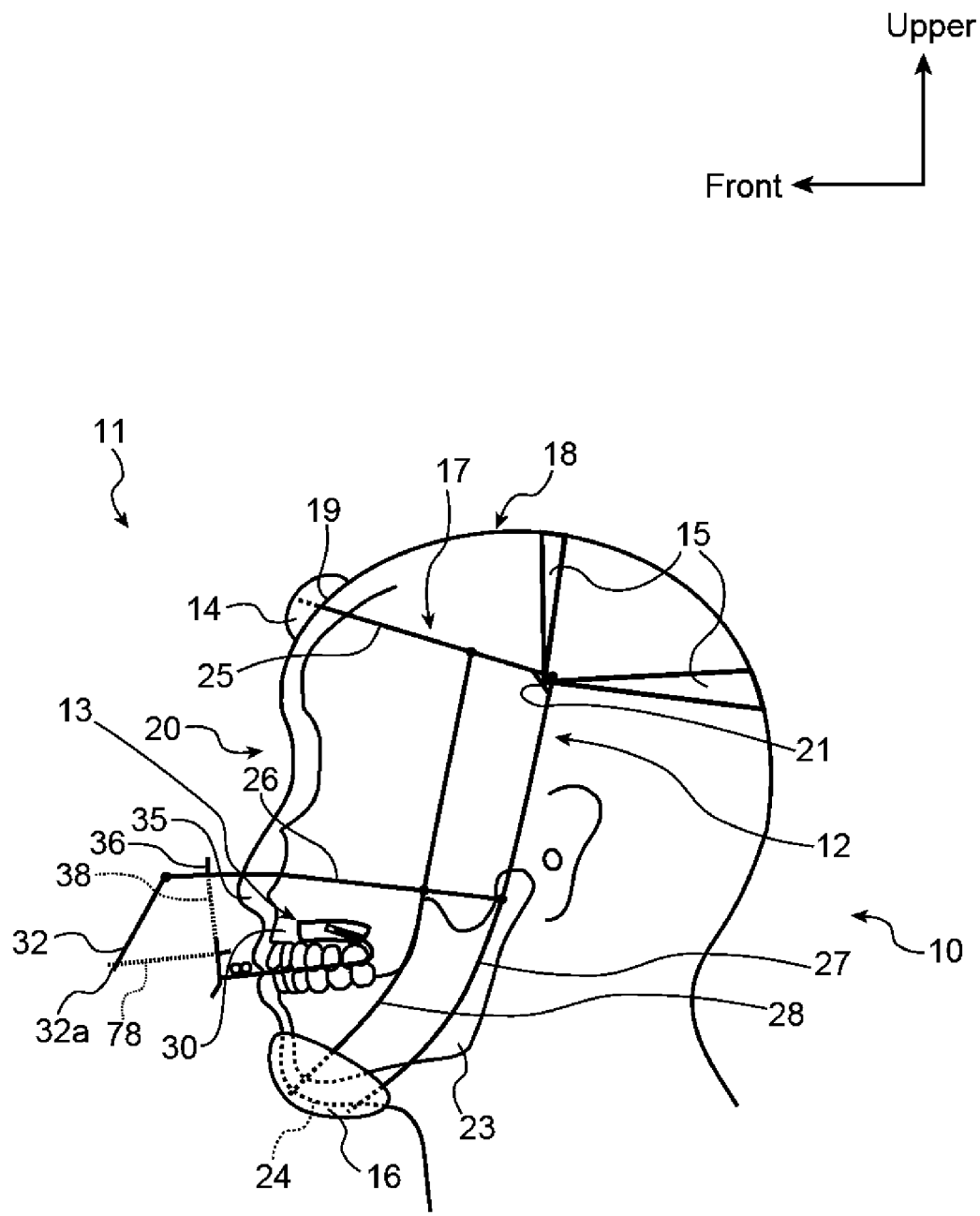
FIG. 1 is a left side view schematically illustrating the entire structure of a maxillofacial orthodontic appliance according to one embodiment of the present invention.

In the following, explanation will be given on a maxillofacial orthodontic appliance according to one embodiment of the present invention, referring to the drawings.

Figure 2:
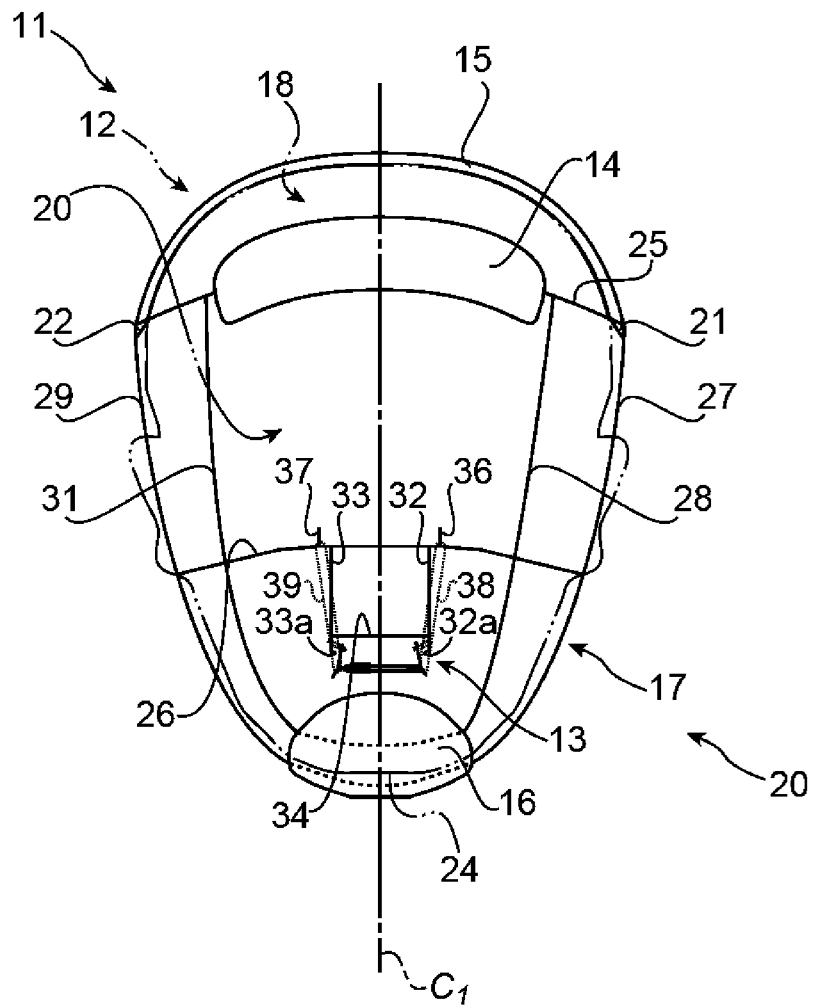
FIG. 2 is a front view schematically illustrating the entire structure of a maxillofacial orthodontic appliance according to one embodiment of the present invention.

As illustrated in FIG. 1 and FIG. 2, the maxillofacial orthodontic appliance 11 mainly comprises a head unit 12 and a mouthpiece unit 13.

The head unit 12 comprises a front head support (head support) 14, a head strap (head support) 15, a chin cap 16 and a metal frame set 17.

Among these, the front head support 14 and the head strap fix the head unit 12 to the head 18 of a human 10.

The front head support 14 is formed of a resin in the shape corresponding to that of the forehead 19 of the human 10. However, a sponge sheet, not shown in the drawings, is affixed on the surface actually contacting the forehead 19.

The head strap 15 is a belt like component formed of a cloth. It can support the head 18 from the upside and backside by means of being inserted into a left ring 21 and a right ring 22, shown in FIG. 2, formed on the metal frame set 17. In addition, the both ends of the head strap 15 can be connected releasably by means of a hook-and-loop fastener (not shown in the drawings).

The chin cap 16 a component formed of a resin, which contacts the lower end 24 of the mandible 23.

The metal frame set 17 comprises the steel frames including: an upper transverse bar 25, a lower transverse bar (horizontal bar) 26, a left-outside vertical bar 27, a left-inside vertical bar 28, a right-outside vertical bar 29, a right-inside vertical bar 31, a left extended bar 32, a right extended bar 33 and an interconnecting bar 34.

Of these, the upper transverse bar 25 is a frame extending in front of the forehead 19 in the width direction (from left to right) of the head 18, of which left end is welded to the upper end of the left-outside vertical bar 27 and right end is welded to the upper end of the right-outside vertical bar 29. About in the middle of the upper transverse bar 25, the above-mentioned front head support 14 is fixed. In addition, to the upper transverse bar 25, the upper end of the left-inside vertical bar 28 is welded at the position closer to the center C1 of the face 20 than the left end of the bar 25, and the upper end of the right-inside vertical bar 31 is welded at the position closer to the center C1 of the face 20 than the right end of the bar 25.

The lower transverse bar 26 is a frame extending from left to right in front of the nose 35, of which left end is welded to around the middle of the left-outside vertical bar 27 and right end is welded to around the middle of the right-outside vertical bar 29. In addition, to the lower transverse bar 26, the midpoint of the left-inside vertical bar 28 is welded at the position closer to the center $C_1$ of the face 20 than the left end of the bar 26, and the midpoint of the right-inside vertical bar 31 is welded at the position closer to the center $C_1$ of the face 20 than the right end of the bar 26.

As shown in FIG. 2, a left sub-B hook (left-second-B projection) 36 is welded to the lower transverse bar 26 at the left side of the face 20, and a right sub-B hook (right-second-B projection) 37 is welded to the lower transverse bar 26 at the right side of the face 20.

On the left sub-B hook 36 and right sub-B hook 37, a left vertical elastic (left-second elastic body) 38 and a right vertical elastic (right-second elastic body) 39 are hooked, respectively. Both of these left vertical elastic 38 and right vertical elastic 39 are ring-shaped elastic bodies which are formed of a rubber.

The left-outside vertical bar 27 is a frame, which constitutes the left end of the metal frame set 17, extending approximately vertically at the left side of the face 20. The lower end of the left-outside vertical bar 27 is located at the position closer to the center $C_1$ of the face 20 than its upper end in the front view shown in FIG. 2.

The left-inside vertical bar 28 is a frame extending approximately vertically at the position closer to the center $C_1$ of the face 20 than the left-outside vertical bar 28. The lower end of the left-inside vertical bar 28 is located at the position closer to the center $C_1$ of the face 20 than its upper end in the front view shown in FIG. 2.

The portions that are lower than the lower transverse bar 26, of both left-outside vertical bar 27 and left-inside vertical bar 28, are formed in the shape of an arc.

The right-outside vertical bar 29 is a frame, which constitutes the right end of the metal frame set 17, extending approximately vertically at the right side of the face 20. The lower end of the right-outside vertical bar 29 is located at the position closer to the center $C_1$ of the face 20 than its upper end, in the front view shown in FIG. 2.

The right-inside vertical bar 31 is a frame extending approximately vertically at the position closer to the center $C_1$ of the face 20 than the right-outside vertical bar 29. The lower end of the right-inside vertical bar 31 is located at the position closer to the center $C_1$ of the face 20 than its upper end, in the front view shown in FIG. 2.

The portions that are lower than the lower transverse bar 26, of both right-outside vertical bar 29 and right-inside vertical bar 31, are formed in the shape of an arc.

The left extended bar (left-B extended bar) 32 is a frame extending from the lower transverse bar 26 in front of and at the left side of the face 20 with its tip 32a being disposed forward of the mouth. The tip (left main-B hook) 32a of the left extended bar 32 is hooked with a left horizontal elastic 78.

The right extended bar (right-B extended bar) 33 is a frame extending from the lower transverse bar 26 in front of and at the right side of the face 20 with its tip 33a being disposed forward of the mouth. The tip (right main-B hook) 33a of the right extended bar 33 is hooked with a right horizontal elastic 79.

The interconnecting bar 34 is a frame extending horizontally, which connects the vicinity of the tip 32a of the left extended bar 32 and the vicinity of the tip 33a of the right extended bar 33.

Next, an explanation will be given on the mouthpiece unit 13.

Figure 3:
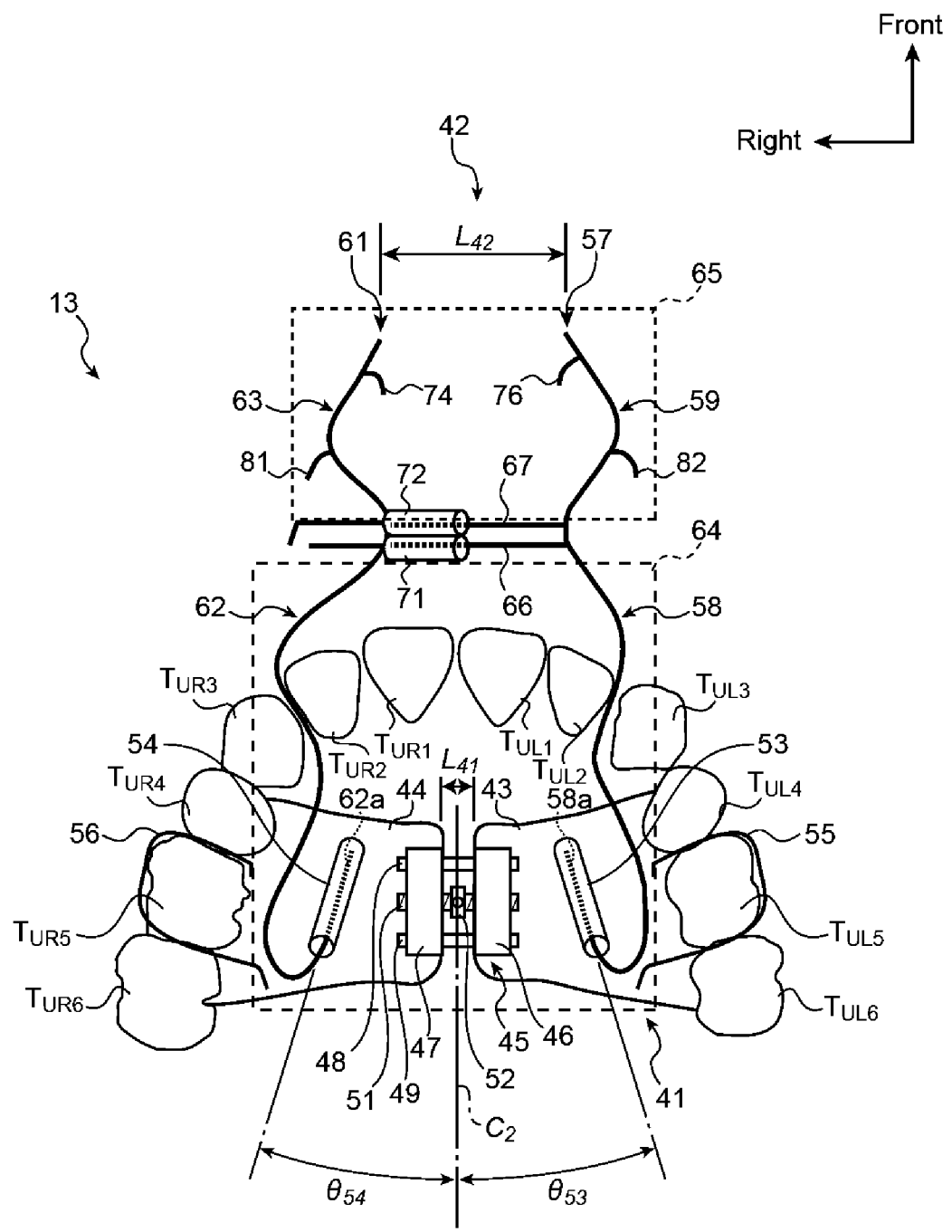
FIG. 3 is a bottom view schematically illustrating the mouthpiece unit of a maxillofacial orthodontic appliance according to one embodiment of the present invention.

As shown in FIG. 3, the mouthpiece unit 13 mainly comprises a maxilla expander 41 and an active bow 42.

Of these, the maxilla expander 41 is fixed to the maxilla 30 in the oral cavity of the human 10 and expands the maxilla 30 in the left and right directions.

This maxilla expander 41 comprises a left floor part (left contact part) 43 and a right floor part (right contact part) 44.

Figure 4:
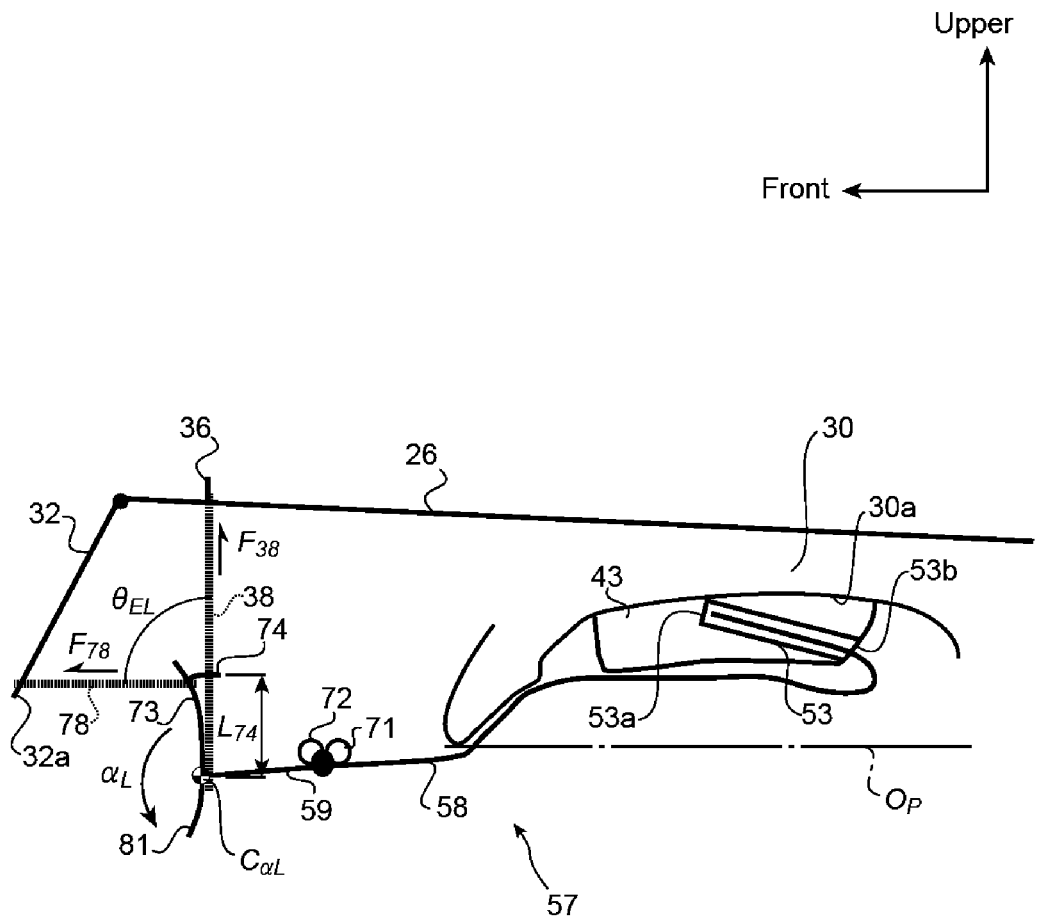
FIG. 4 is a side view schematically illustrating the left side of the mouthpiece unit of a maxillofacial orthodontic appliance according to one embodiment of the present invention.

The left floor part 43 is a component contacting the under surface 30a of the maxilla 30 as shown in FIG. 4 and pushing the left maxilla fourth tooth $T_{UL4}$, left maxilla fifth tooth $T_{UL5}$ and left maxilla sixth tooth $T_{UL6}$ of the left maxillary tooth row from within as shown in FIG. 3.

Figure 5:
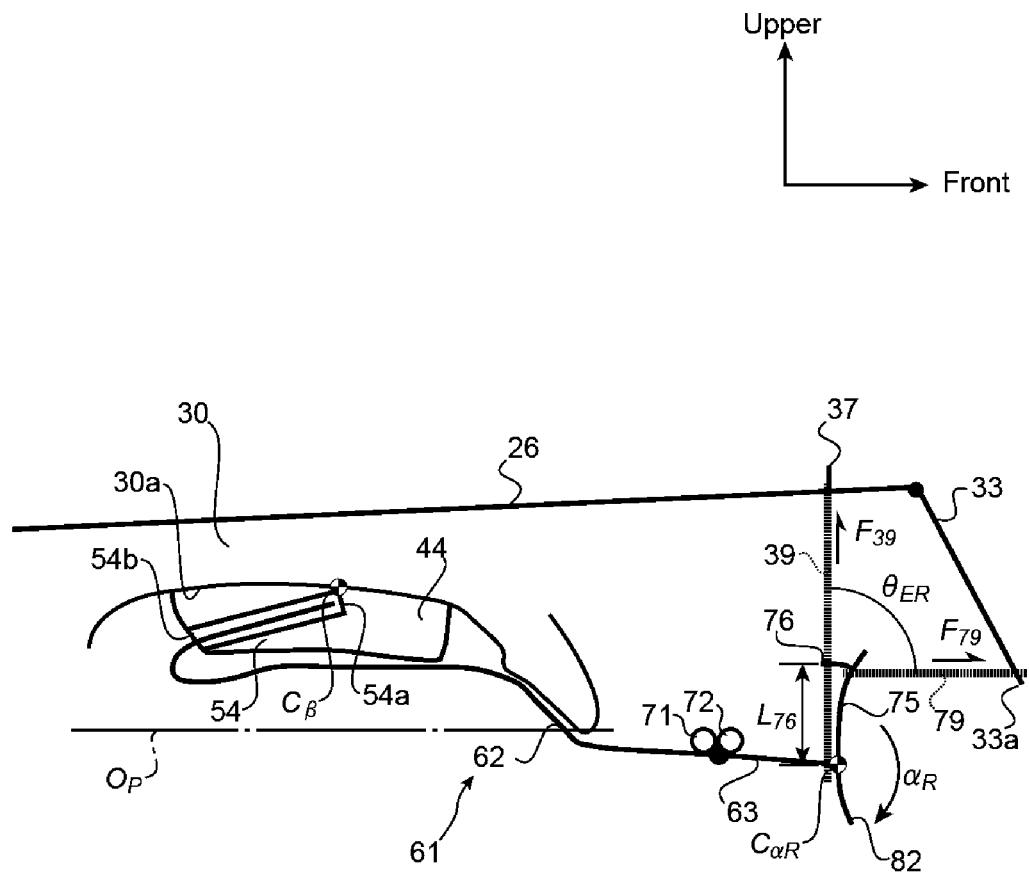
FIG. 5 is a side view schematically illustrating the right side of the mouthpiece unit of a maxillofacial orthodontic appliance according to one embodiment of the present invention.

The right floor part 44 is a component contacting the under surface 30a of the maxilla 30 as shown in FIG. 5 and pushing the right maxilla fourth tooth $T_{UR4}$, right maxilla fifth tooth $T_{UR5}$ and right maxilla sixth tooth $T_{UR6}$ of the right maxillary tooth row from within as shown in FIG. 3.

These left floor part 43 and right floor part 44 are formed of a resin and interconnected to each other with an expansion screw mechanism (adjusting mechanism) 45.

The expansion screw mechanism 45 comprises a left block 46 embedded in the left floor part 43, a right block 47 embedded in the right floor part 44, a pair of shafts 48, 49 interconnecting the left and right blocks 46, 47 and an expansion screw 51 provided between the pair of shafts 48, 49 and allowing fine adjustment of the distance $L_{41}$ between the left and right blocks 46, 47. In the result, the expansion screw mechanism 45 can vary the width $L_{41}$ of the maxilla expander 41 (namely, the distance between the left floor part 43 and the right floor part 44) freely.

To the center of the expansion screw 51, a ring 52 to be engaged with a tool (not shown in the drawings) is fixed.

By rotating the ring 52 using the tool, the distance $L_{41}$ between the left and right blocks 46, 47 can be changed. In such a case, the left and right blocks 46, 47 can slide relative to the pair of shafts 48, 49.

The range of motion of the expansion screw mechanism 45 is about 11 mm at the maximum. However, around 8 mm to 9 mm is appropriate from a practical standpoint.

A left sliding tube (left hole) 53 is embedded in the left floor part 43. On the other hand, a right sliding tube (right hole) 54 is embedded in the right floor part 54. Both of these left and right sliding tubes 53, 54 are cylinders made of stainless steel. Incidentally, they can be made of such metals as titanium, aluminium and so on, other than stainless steel.

In addition, on the left floor part 43, a left latch 55 for holding the left maxilla fifth tooth $T_{UL5}$ is provided. On the other hand, on the right floor part 44, a right latch 56 for holding the right maxilla fifth tooth $T_{UR5}$ is provided.

The back ends 53b, 54b of the left sliding tube 53 and the right sliding tube 54 both communicate with inside the oral cavity.

On the other hand, the front end 53a of the left sliding tube 53 is blocked by the left floor part 43, and the front end 54a of the right sliding tube 54 is blocked by the right floor part 44.

In the plan view shown in FIG. 3, the left sliding tube 53 is inclined at a predetermined angle $\theta_{53}$, relative to the center line $C_2$ of the maxilla expander 41, and the right sliding tube 54 is inclined at a predetermined angle $\theta_{54}$, relative to the center line $C_2$ of the maxilla expander 41. Though, in this case, the angles $\theta_{53}$ and $\theta_{54}$ are set to have the same absolute values, they may be modified as appropriate depending on the shape of the oral cavity.

In addition, in the left side view shown in FIG. 4, in which the left floor part 43 of the maxilla expander 41 is fixed to the maxilla 30, the left sliding tube 53 is disposed being inclined with its back end 53b is located lower than the front end 53a.

In the same way, in the right side view shown in FIG. 5, in which the right floor part 44 of the maxilla expander 41 is also fixed to the maxilla 30, the right sliding tube 54 is disposed being inclined with its back end 54b is located lower than the front end 54a.

Into the back end 53b of the left sliding tube 53, the back end 58a of a left wire 57 of the active bow 42 can be inserted. On the other hand, into the back end 54b of the right sliding tube 54, the back end 62a of a right wire 61 can be inserted.

The left wire 57 mainly comprises a left inner bow 58 and a left outer bow 59. The right wire 61 mainly comprises a right inner bow 62 and a right outer bow 63. Incidentally, the left inner bow 58 and the right inner bow 61 are referred to simply as "inner bow 64" in combination. Incidentally, the left outer bow 59 and the right outer bow 63 are referred to as "outer bow 65" in combination.

Figure 6:
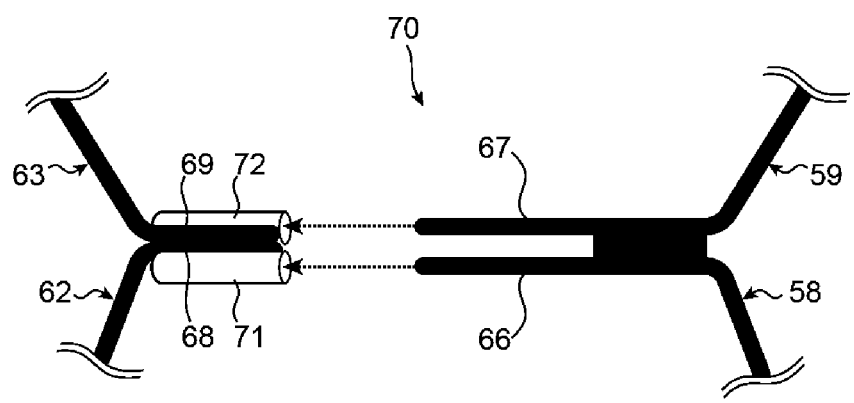
FIG. 6 is a schematic diagram illustrating the vicinity of the active bow tube of the mouthpiece unit in a maxillofacial orthodontic appliance according to one embodiment of the present invention.
Figure 7:
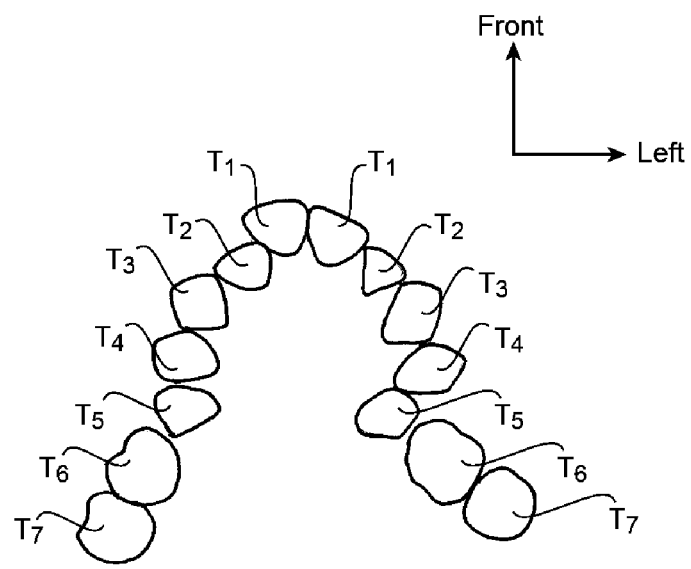
FIG. 7 are schematic diagrams illustrating an example of an orthodontic treatment by means of a conventional distal movement of the teeth.
Figure 7:
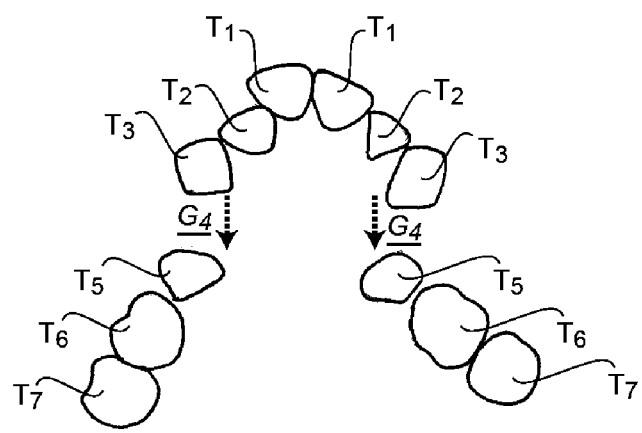
Figure 7:
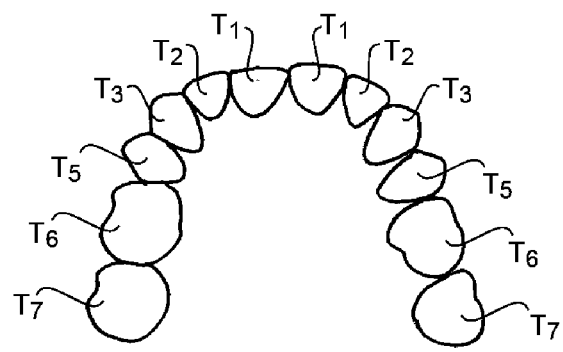
Figure 8:
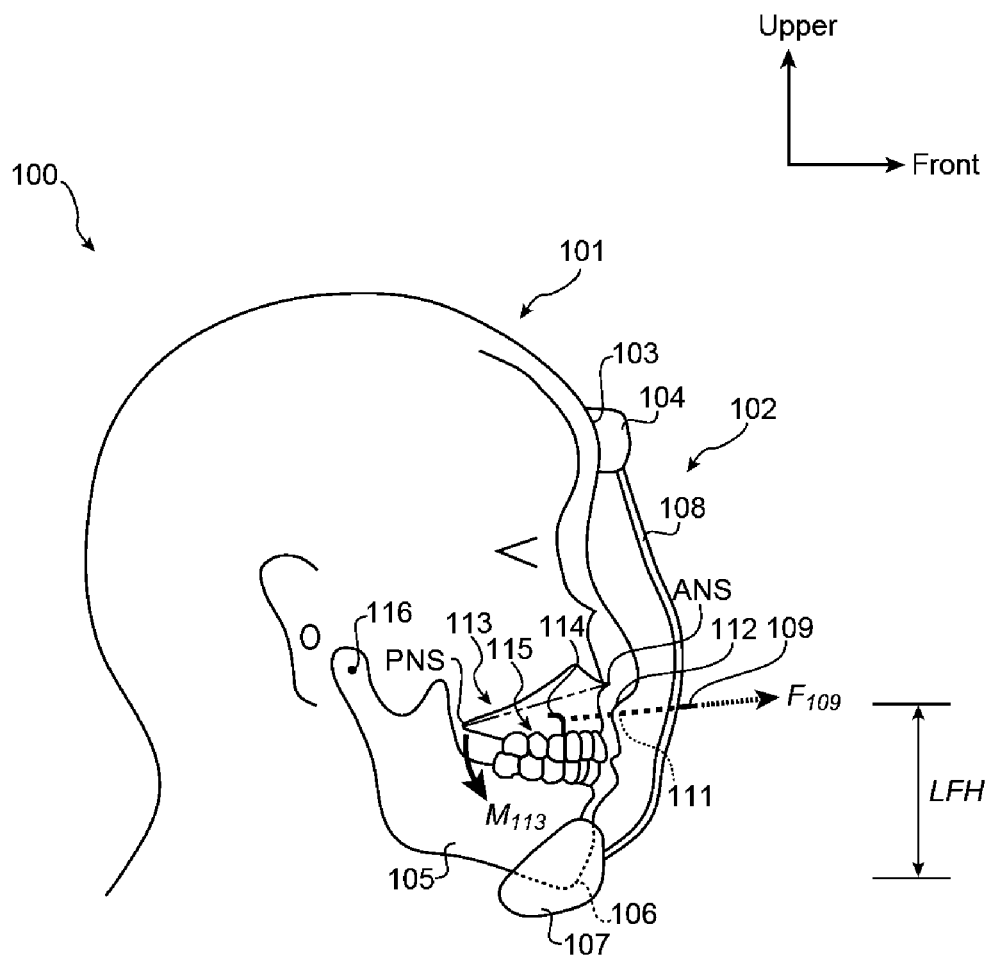
FIG. 8 is a view schematically illustrating an example of a conventional maxillofacial orthodontic appliance.
Figure 9:
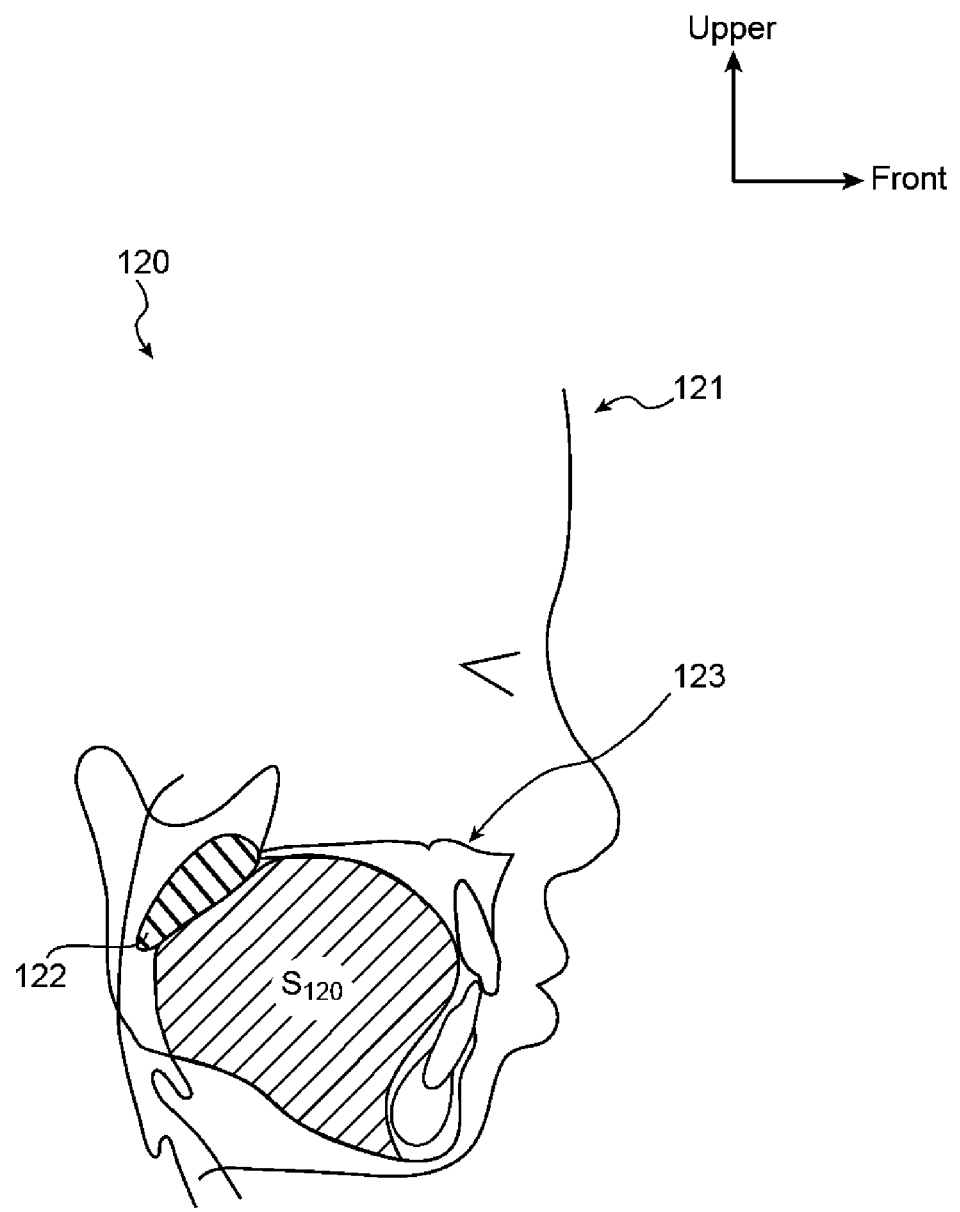
FIG. 9 is a side view schematically illustrating the oral cavity of a general person who does not suffer from malocclusion.
Figure 10:
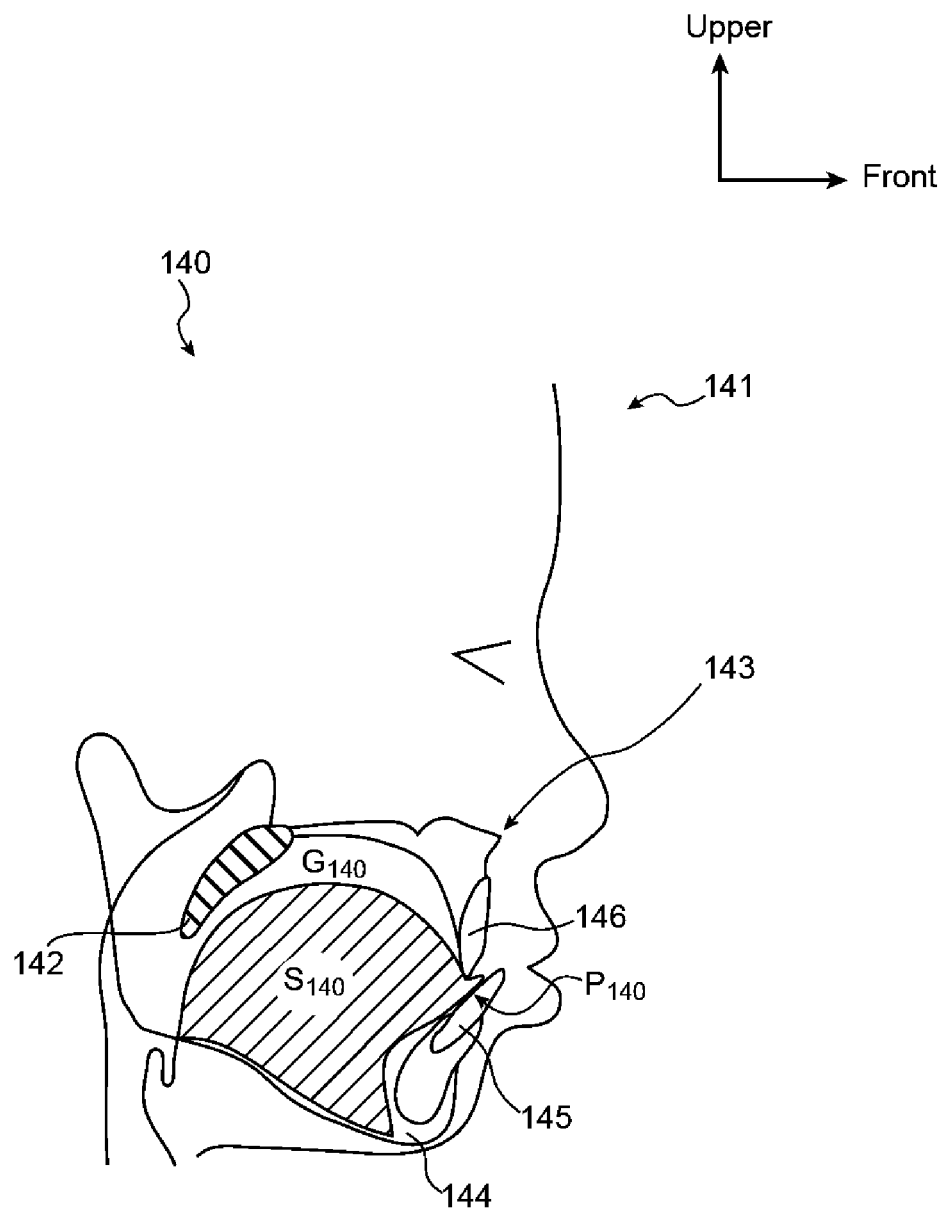
FIG. 10 is a side view schematically illustrating the oral cavity of a general person who suffers from mandibular protrusion.
Figure 11:
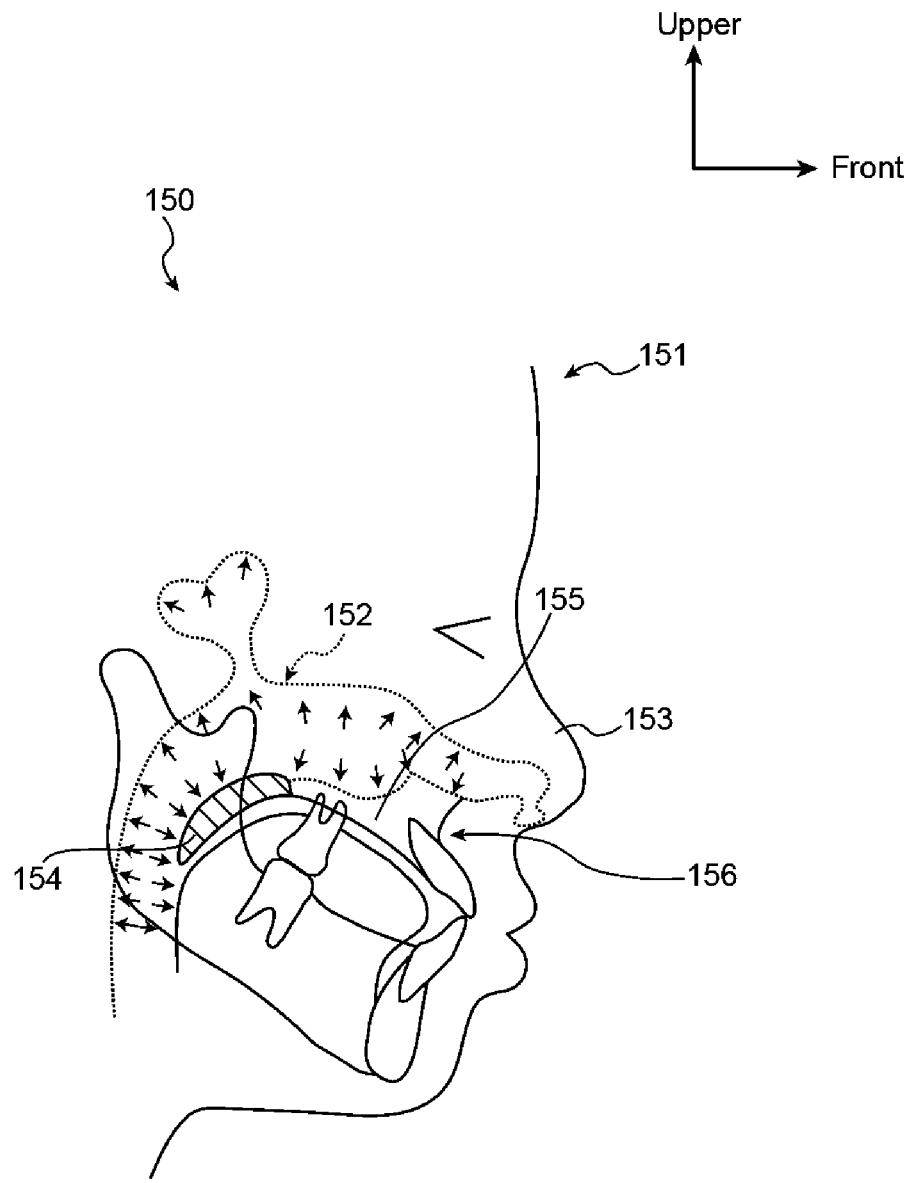
FIG. 11 is a schematic view mainly illustrating the paranasal sinus of a person.
Figure 12:
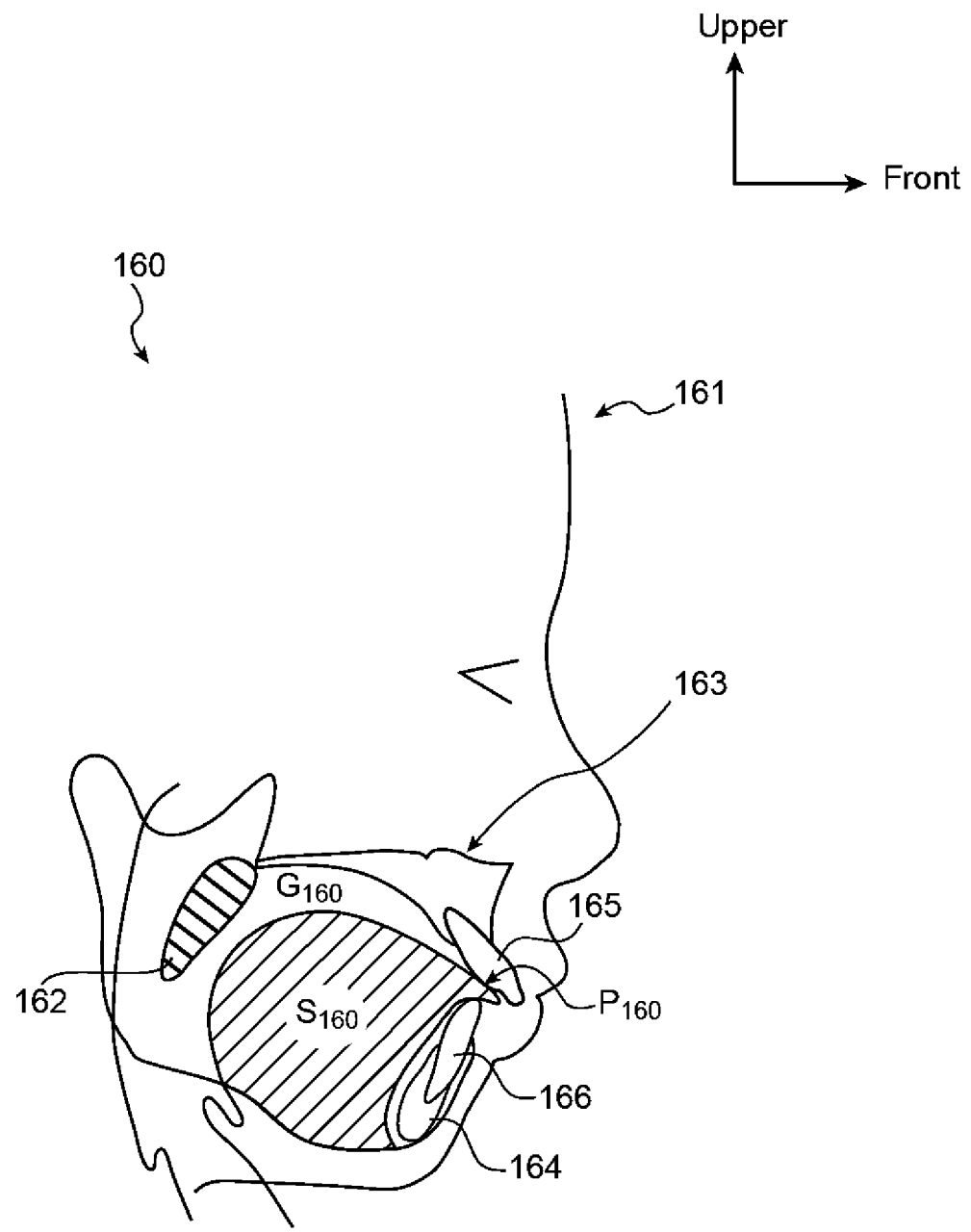
FIG. 12 is a side view schematically illustrating the oral cavity of a general person who suffers from maxillary protrusion.

The interconnecting part of the inner bow 64 and the outer bow 65 is shown in FIG. 6.

As shown in FIG. 6, the front end portion (connecting wire) 66 of the left inner bow 57 and the back end portion (connecting wire) 67 of the left outer bow 59 are both extended straight from left to right and are welded to each other.

In the same way, the front end portion 68 of the right inner bow 62 and the back end portion 69 of the right outer bow 63 are both extended straight from left to right and are welded to each other. In addition, to the front end portion 68 of the right inner bow 62 and the back end portion 69 of the right outer bow 63, a pair of active bow tubes (connecting tubes) 71, 72 are welded. Incidentally, these welded parts are coated with silver solder. In place of silver solder, palladium solder or gold solder may be used.

One of the pair of active bow tubes 71, 72 will be referred to as inner-side active bow tube 71, and the other will be referred to as outer-side active bow tube 72. Both of these inner-side active bow tube 71 and outer-side active bow tube 72 open at both ends.

The front end portion 66 of the left inner bow 58 is inserted slidably into and passes through the inner-side active bow tube 71.

The back end portion 67 of the left outer bow 59 is inserted slidably into and passes through the outer-side active bow tube 72.

These inner-side active bow tube 71, outer-side active bow tube 72, front end portion 66 of the left inner bow 58 and back end portion 67 of the left outer bow 59 constitute a slidable mechanism 70. This slidable mechanism 70 enables to vary the width of the active bow 42, namely, the distance $L_{42}$ (refer to FIG. 3) between the left wire 57 and the right wire 61 freely.

These active bow tubes 71, 72 have the same inner diameters (for example, in the order of 1.6 mm).

On the other hand, the front end portion 66 of the left inner bow 58 has the first external diameter (for example, in the order of 1.5 mm) which is a little smaller than the inner diameter of the active bow tube 71.

In addition, the back end portion 67 of the left outer bow 59 has the second external diameter (for example, in the order of 1.3 mm) which is a little smaller than the above-mentioned first external diameter.

As shown in FIG. 4, a left-A tip wire 73 sticking out upward is welded to the front end of the left outer bow 59.

To the vicinity of the upper end of the left-A tip wire 73, a left main-A hook (left-first-A projection) projecting backward (in the direction toward the face 20) is welded.

As shown in FIG. 5, a right-A tip wire 75 sticking out upward is welded to the front end of the right outer bow 63.

To the vicinity of the upper end of the right-A tip wire 75, a right main-A hook (right-first-A projection) projecting backward (in the direction toward the face 20) is welded.

These left main-A hook 74 and right main-A hook 76 are hooked with a left horizontal elastic (left-first elastic body) 78 and a right horizontal elastic (right-first elastic body) 79, respectively. Both of these left horizontal elastic and right horizontal elastic 79 are ring-shaped elastic bodies which are formed of a rubber. By these left horizontal elastic 78 and right horizontal elastic 79, the left main-A hook 74 and the right main-A hook 76 can be biased forward.

The biasing force $F_{78}$ of the left horizontal elastic 78 can produce a moment $\alpha_L$ of which rotation center $C_{\alpha L}$ is the connecting portion between the left outer bow 59 and the left-A tip wire 73. The biasing force $F_{79}$ of the right horizontal elastic 79 can produce a moment $\alpha_R$ of which rotation center $C_{\alpha R}$ is the connecting portion between the right outer bow and the right-A tip wire 75.

The height $L_{74}$ from the connecting portion between the left outer bow 59 and the left-A tip wire 73 to the left main-A hook 74 is decided depending on the magnitude of the moment $\alpha_L$. In the same way, the height $L_{76}$ from the connecting portion between the right outer bow 63 and the right-A tip wire 75 to the right main-A hook 76 is decided depending on the magnitude of the moment $\alpha_R$.

As shown in FIG. 4, a left sub-A hook (left-second-A projection) 81 sticking out downward is welded to the front end of the left outer bow 59.

In the same way, as shown in FIG. 5, a right sub-A hook (right-second-A projection) 82 sticking out downward is welded to the front end of the right outer bow 63.

On these left sub-A hook 81 and right sub-A hook 82, the left vertical elastic 38 and the right vertical elastic will be hooked, respectively. In addition, as described earlier, these left vertical elastic 38 and right vertical elastic 39 are hooked on the left sub-B hook 36 and the right sub-B hook 37 that are welded on the lower transverse bar 26, respectively. In the result, by these left vertical elastic 38 and right vertical elastic 39, the left sub-A hook 81 and the right sub-A hook 82 can be biased upward.

Moreover, as shown in FIG. 4, the extension direction of the left horizontal elastic 78, namely, the direction in which the biasing force $F_{78}$ of this left horizontal elastic 78 acts, and the extension direction of the left vertical elastic 38, namely, the direction in which the biasing force $F_{38}$ of this left vertical elastic 38 acts, are set to be approximately orthogonal to each other (namely, $\theta_{EL}$ is nearly equal to 90°).

In the same way, as shown in FIG. 5, the extension direction of the right horizontal elastic 79, namely, the direction in which the biasing force $F_{79}$ of this right horizontal elastic 79 acts, and the extension direction of the right vertical elastic 39, namely, the direction in which the biasing force $F_{39}$ of this right vertical elastic 39 acts, are set to be approximately orthogonal to each other (namely, $\theta_{ER}$ is nearly equal to 90°).

The maxillofacial orthodontic appliance according to one embodiment of the present invention exhibits the following operations and effects, since it has a construction described above.

When using the maxillofacial orthodontic appliance of the present invention, first, the back end 58a of the left inner bow 58 is inserted into the left sliding tube 53 and the back end 62a of the right inner bow 62 is inserted into the right sliding tube 54. By such a procedure, the active bow 42 is integrated with the maxilla expander 41, thereby forming the mouthpiece unit 13.

At this time, the distance $L_{41}$ between the left floor part 43 and the right floor part 44 can be adjusted using the expansion screw mechanism 45. The width $L_{42}$ of the active bow 42 is changed accompanying the variation of the distance $L_{41}$ between the left floor part 43 and the right floor part 44, by means of the slidable mechanism 70.

In the result, the user is free from the care about the width $L_{42}$ of the active bow 42, and the width of the mouthpiece unit 13 can be set at any appropriate value just by adjusting the distance $L_{41}$ between the left floor part 43 and the right floor part 44.

The width of the maxilla expander 41 gets larger as the treatment stage progresses. Specifically speaking, the distance $L_{41}$ between the left floor part 43 and the right floor part 44 gets larger as the width of the maxilla 30 gets large. Even in such a stage, it is not necessary for the user to change the width $L_{42}$ of the active bow 42 in particular. This is because the width $L_{42}$ of the active bow 42 changes accompanying the variation of the distance $L_{41}$ of the maxilla expander 41, as described above.

In addition, as shown in FIG. 6, the front end portion of the left inner bow 58 has the first external diameter (for example, in the order of 1.5 mm) which is a little smaller than the inner diameter (for example, 1.6 mm) of the active bow tubes 71, 72, in the slidable mechanism 70. On the other hand, the back end portion 67 of the left outer bow 59 has the second external diameter (for example, in the order of 1.3 mm) which is a little smaller than the above-mentioned first external diameter.

With such a structure, the active bow tubes 71, 72 of the right wire 61 can slide, relative to the front end portion 66 of the left inner bow 58 and the back end portion 67 of the left outer bow 59, with an appropriate magnitude of friction force. This enables an appropriate interconnection of the left wire 57 and the right wire 61, allowing the variation of the width $L_{42}$ of the active bow 42.

On the back end portion 67 of the left outer bow 59, a slight play is provided relative to the active bow tube 72. Therefore, the left wire 57 and the right wire 61 are allowed to be twisted relative to each other. Such a construction makes it easier for the back end 58a of the left inner bow 58 and the back end 62a of the right inner bow 62 to be inserted into the left sliding tube 53 and the right sliding tube 54, respectively. This then makes it easier for the active bow 42 to be integrated with the maxilla expander 41.

In addition, the front end portion 66 of the left inner bow 58 inserted into the inner-side active bow tube 71 passes through the inner-side active bow tube 71, and the back end portion 67 of the left outer bow 59 inserted into the outer-side active bow tube 72 passes through the outer-side active bow tube 72.

Such a construction makes it possible to prevent the easy untying of the interconnection between the left wire 57 and the right wire 61, even with considerable change in the width of the maxilla expander 41 or twist of the left wire 57 relative to the right wire 61.

Subsequently, the head unit 12 is fixed to the head 18.

In this case, first, the chin cap 16 is kept in contact with the lower end portion 24 of the mandible 23 and, at the same time, the front head support 14 is kept in contact with the forehead 19. At this moment, the head straps 15 are inserted into the left ring 21 and the right ring 22 which are formed on the metal frame set 17.

Then, as shown in FIG. 1, the head straps 15 are disposed in contact with the top and the back of the head 18, and the both ends of the head strap 15 are interconnected by means of hook-and-loop fasteners (not shown in the drawings).

This enables the fixation of the head unit 12 to the head 18 and prevents slippage of the head unit 12 from the head 18 even when a certain magnitude of force acts on the head unit 12.

Then, the mouthpiece unit 13 is fixed to the maxilla 30. At the same time, with the head unit 12 fixed to the head 18, the mouthpiece unit 13 and the head unit 12 are interconnected with the left horizontal elastic 78, right horizontal elastic 79, left vertical elastic 38 and right vertical elastic 39.

More specifically, as shown in FIG. 4, the left horizontal elastic 78 is hooked on the left main-A hook 74 of the mouthpiece unit 13 and also on the tip 32a of the left extended bar 32 of the head unit 12. In addition, as shown in FIG. 5, the right horizontal elastic 79 is hooked on the right main-A hook 76 of the mouthpiece unit 13 and also on the tip 33a of the right extended bar 33 of the head unit 12.

In this way, the biasing force $F_{78}$ of the left horizontal elastic 78 produces the moment $\alpha_L$ of which rotation center $C_{\alpha L}$ is the connecting portion between the left outer bow 59 and the left-A tip wire 73. On the other hand, the biasing force $F_{79}$ of the right horizontal elastic 79 produces the moment $\alpha_R$ of which rotation center $C_{\alpha R}$ is the connecting portion between the right outer bow 63 and the right-A tip wire 75.

This enables not only a forward growth of the maxilla 30 but also an upward lift of the maxilla 30 due to an intensive upward lift of the maxilla expander 41, which leads to securing a space in which the tongue can be settled in the state that it is kept in contact with the under surface of the maxilla 30.

However, the above-mentioned moments $\alpha_L$, $\alpha_R$ that are excessively large can not promote the proper growth of the maxilla 30. Moreover, this may lead to the liability to detachment of the maxilla expander 41 from the maxilla 30.

In order to prevent that, the left vertical elastic 38 is hooked on the left sub-A hook 81 of the mouthpiece unit and also on the left sub-B hook 36 of the head unit 12. In addition, the right vertical elastic 39 is hooked on the right sub-A hook 82 of the mouthpiece unit 13 and also on the right sub-B hook 37 of the head unit 12.

Such a construction makes it possible to suppress the moment $\alpha_L$ induced by the biasing force $F_{78}$ of the left horizontal elastic 78 and the moment $\alpha_R$ induced by the biasing force $F_{79}$ of the right horizontal elastic 79 properly.

In addition, in the present embodiment, the relationship between the biasing force $F_{78}$ (for example, about 300 g) of the left horizontal elastic 78 and the biasing force $F_{38}$ (for example, about 100 g) of the left vertical elastic 38 is set to satisfy the formula (1) below. In the same way, the relationship between the biasing force $F_{79}$ (for example, about 300 g) of the right horizontal elastic 79 and the biasing force $F_{39}$ (for example, about 100 g) of the right vertical elastic 39 is set to satisfy the formula (2) below.

$$F_{78}:F_{38}=3:1 \quad (1)$$

$$F_{79}:F_{39}=3:1 \quad (2)$$

In addition, the left horizontal elastic 78 and the right horizontal elastic 79 are both disposed parallel to the direction in which the occlusal plane OP (refer to FIG. 4 and FIG. 5) extends. The angle $\theta_{EL}$ which the left horizontal elastic 78 and the left vertical elastic 38 form is set at about 90°. In the same way, the angle $\theta_{ER}$ which the right horizontal elastic 79 and the right vertical elastic 39 form is also set at about 90°.

In this way, a space can be secured in which the tongue is settled in the state that it is kept in contact with the under surface of the maxilla 30 and thus nasal breathing, not mouth breathing, can be carried out naturally. Furthermore, the nasal breathing can increase the internal pressure of the paranasal sinus (namely, it can produce a positive pressure) which can lead to the acceleration of further development of the maxilla 30.

In the appliance of the present invention, the tooth low may seem to be corrected by means of pressing the teeth directly. But instead, it promotes a proper growth of the maxilla 30 (especially, forward growth thereof). The proper forward development of the maxilla 30 can then secure the space of teeth eruption, and thereby, the tooth row can be corrected. This can then lead to the correction of the malocclusion.

Furthermore, a proper development of the maxilla 30 can stimulate a proper development of the mandible 23 (especially, a forward development thereof). Therefore, not only the tooth low of the maxilla 30 but also the tooth low of the mandible 23 can be corrected.

Namely, not only maxillary protrusion but also mandibular protrusion can be corrected.

There is another advantageous effect of sufficiently enabling a teeth movement to a consider able extent (for example, a movement in the order of 20 mm), which has been impossible in the orthodontic treatment by means of a distal movement, which was described in the section of BACKGROUND OF THE INVENTION.

Moreover, using the appliance of the present invention exhibits another advantageous effect of securing higher safety and cost efficiency, due to no need for extraction in principle.

An embodiment and its variations of the present invention have been explained above. It is to be understood that the present invention is not limited to those and various modifications can be added thereto so long as they do not depart from the scope of the present invention.

In the embodiment described above, the explanation was given on an example in which the metal frame set 17 of the head unit 12 is constructed symmetrical with the center line $C_1$ of the face 20 being the axis. However, the present invention is not limited to such a construction. For example, the metal frame set 17 of the head unit 12 may be constructed so that the shape thereof corresponds to the shape of the head 18 or the face 20 of the human 10. In addition, it may be constructed asymmetrically with the center line $C_1$ of the face 20 being the axis.

In addition, in the embodiment described above, the explanation was given on a case in which a pair of active bow tubes 71, 72 are welded to the right wire 61, the front end portion 66 of the left inner bow 58 is inserted into the inner-side active bow tube 71, and the back end portion 67 of the left outer bow 59 is inserted into the outer-side active bow tube 72. However, the present invention is not limited to such a construction. For example, it is also possible that a pair of active bow tubes 71, 72 are welded to the left wire 57, the front end portion (not shown in the drawings) of the right inner bow 62 is inserted into the inner-side active bow tube 71, and the back end portion (not shown in the drawings) of the right outer bow 63 is inserted into the outer-side active bow tube 72.

In addition, in the embodiment described above, the explanation was given on an example in which the left sub-B hook (left-second-B projection) 36 and the right sub-B hook (right-second-B projection) 37 are welded to the lower transverse bar 26, as shown in FIG. 2. However, the present invention is not limited to such a construction. For example, these left sub-B hook 36 and the right sub-B hook 37 are provided on a frame for a sub-hook (not shown in the drawings) which extends downward from the lower transverse bar 26.

In addition, in the embodiment described above, the explanation was given on a case in which a pair of active bow tubes 71, 72 are used. However, the present invention is not limited to such a construction. For example, only one active bow tube may be provided, in consideration of the rigidities of the active bow tube and the component (connecting wire) inserted into the active bow tube. Or otherwise, three or more of active bow tubes may be provided.

In addition, in the embodiment described above, the explanation was given on an example in which the inner diameters of the pair of active bow tubes 71, 72 are set at about 1.6 mm, the external diameter (the first external diameter) of the front end portion 66 of the left inner bow 58 is set at about 1.5 mm, and the external diameter (the second external diameter) of the back end portion 67 of the left outer bow 59 is set at about 1.3 mm. However, the present invention is not limited to such a construction.

For example, it is also possible that the external diameter of the front end portion 66 of the left inner bow 58 is set at about 1.5 mm to 1.55 mm, and the external diameter of the back end portion 67 of the left outer bow 59 is set at about 1.45 mm to 1.35 mm.

In addition, in the embodiment described above, the explanation was given on a case in which the angle $\theta_{EL}$ which the left horizontal elastic 78 and the left vertical elastic 38 form is set at about 90°, and the angle $\theta_{ER}$ which the right horizontal elastic 79 and the right vertical elastic 39 form is set at about 90°. In this context, "about 90°" does not mean that it should be 90° strictly, but it may fall within the range of from 80° to 100° in the practical use.

In addition, in the embodiment described above, the explanation was given on an example in which the relationship between the biasing force $F_{78}$ of the left horizontal elastic 78 and the biasing force $F_{38}$ of the left vertical elastic 38 is set to satisfy the above-mentioned formula (1) and, in the same way, the relationship between the biasing force $F_{79}$ of the right horizontal elastic 79 and the biasing force $F_{39}$ of the right vertical elastic 39 is set to satisfy the above-mentioned formula (2). However, the present invention is not limited to such a construction. For example, the biasing force $F_{78}$ and the biasing force $F_{79}$ may be adjusted to satisfy the formula (3) below, and the biasing force $F_{79}$ and the biasing force $F_{39}$ may be adjusted to satisfy the formula (4) below. However, the biasing force $F_{78}$ or $F_{79}$ that is adjusted to be excessively large would make it difficult to accelerate the proper growth of the maxilla 30. Therefore, the following formulae (3) and (4) should be satisfied.

$$F_{78}:F_{38}=3 \text{ to } 5:1 \quad (3)$$

$$F_{79}:F_{39}=3 \text{ to } 5:1 \quad (4)$$

From the invention thus described, it will be obvious that the same may be varied in many ways. Such variations are not regarded as a departure from the spirit and scope of the invention, and all such modifications as would be obvious to one skilled in the art are intended to be included within the scope of the following claims.

What is claimed is:

1. A maxillofacial orthodontic appliance comprising: a maxilla expander which is adapted to be fixed to the maxilla in the mouth of a human and a towed-unit to be towed which is connected to said maxilla expander and towed in an anterior direction from the human, wherein
said maxilla expander comprises:
a left contact part for pushing the left maxillary tooth row of the human from within,
a right contact part for pushing the right maxillary tooth row of the human from within,
an adjusting mechanism connecting said left contact part and said right contact part with the distance between said left contact part and said right contact part being variable,
a left hole formed on said left contact part and
a right hole formed on said right contact part, and
said towed-unit comprises:
a left wire whose one end is inserted into said left hole and the other end is for protruding out of the mouth,
a right wire whose one end is inserted into said right hole and the other end is for protruding out of the mouth,
a connecting tube provided on one of said left wire and said right wire and extending in the direction of the variation of the distance, caused by said adjusting mechanism, between said left contact part and said right contact part and
a connecting wire provided on the other of said left wire and said right wire and inserted into said connecting tube slidably.

2. A maxillofacial orthodontic appliance according to claim 1 further comprising:
a left-A tip wire provided in the vicinity of the tip of said left wire and sticking out upward,
a right-A tip wire provided in the vicinity of the tip of said right wire and sticking out upward,
a left-first-A projection provided on said left-A tip wire and for projecting toward the face of the human and
a right-first-A projection provided on said right-A tip wire and for projecting toward the face of the human,
said left-first-A projection being hooked with a left-first elastic body which tows said left wire anteriorly and horizontally, and
said right-first-A projection being hooked with a right-first elastic body which tows said right wire anteriorly and horizontally.

3. A maxillofacial orthodontic appliance according to claim 2, wherein
said connecting tube opens at both ends, and
said connecting wire passes through said connecting tube.

4. A maxillofacial orthodontic appliance according to claim 3, wherein
a pair of said connecting tubes are provided on one of said left wire and said right wire, and
a pair of said connecting wires are provided on the other of said left wire and said right wire.

5. A maxillofacial orthodontic appliance according to claim 3, wherein
a pair of said connecting tubes have the same inner diameters,
one of said pair of connecting wires has the first external diameter which is smaller than the inner diameter of said connecting tubes in 0.1 to 0.05 mm, and
the other of said pair of connecting wires has the second external diameter which is smaller than the first external diameter.

6. A maxillofacial orthodontic appliance according to claim 4 comprising:
a head support adapted to be fixed to the head of the human,
a chin support adapted to be fixed to the mandible of the human,
a pair of side frames extending in the vertical direction, of which upper end is connected to said head support and lower end is connected to said chin support,
a horizontal bar for extending from left to right in front of the face of the human at higher position than the mouth of the human and connecting said pair of side frames,
a left-B extended bar for extending from said horizontal bar in front of and at the left side of the face with its tip being disposed forward of the mouth,
a right-B extended bar for extending from said horizontal bar in front of and at the right side of the face with its tip being disposed forward of the mouth, a left-first-B projection provided in the vicinity of the tip of said left-B extended bar and hooked with said left-first elastic body and a right-first-B projection provided in the vicinity of the tip of said right-B extended bar and hooked with said right-first elastic body, said left-first elastic body connecting said left-first-A projection and said left-first-B projection, and said right-first elastic body connecting said right-first-A projection and said right-first-B projection.

7. A maxillofacial orthodontic appliance according to claim 5 comprising:

a head support adapted to be fixed to the head of the human, a chin support adapted to be fixed to the mandible of the human, a pair of side frames extending in the vertical direction, of which upper end is connected to said head support and lower end is connected to said chin support, a horizontal bar for extending from left to right in front of the face of the human at higher position than the mouth of the human and connecting said pair of side frames, a left-B extended bar adapted to be extended from said horizontal bar in front of and at the left side of the face with its tip being disposed forward of the mouth, a right-B extended bar adapted to be extended from said horizontal bar in front of and at the right side of the face with its tip being disposed forward of the mouth, a left-first-B projection provided in the vicinity of the tip of said left-B extended bar and hooked with said left-first elastic body and a right-first-B projection provided in the vicinity of the tip of said right-B extended bar and hooked with said right-first elastic body, said left-first elastic body connecting said left-first-A projection and said left-first-B projection, and said right-first elastic body connecting said right-first-A projection and said right-first-B projection.

8. A maxillofacial orthodontic appliance according to claim 6 comprising:

a left-second-A projection provided in the vicinity of the tip of said left wire and sticking out downward, a right-second-A projection provided in the vicinity of the tip of said right wire and sticking out downward, a left-second-B projection adapted to be connected to said horizontal bar at the left side of the face and sticking out upward, a right-second-B projection adapted to be connected to said horizontal bar at the right side of the face and sticking out upward, a left-second elastic body connecting said left-second-A projection and said left-second-B projection and biasing said left-second-A projection upward and a right-second elastic body connecting said right-second-A projection and said right-second-B projection and biasing said right-second-A projection upward.

9. A maxillofacial orthodontic appliance according to claim 7 comprising:

a left-second-A projection provided in the vicinity of the tip of said left wire and sticking out downward, a right-second-A projection provided in the vicinity of the tip of said right wire and sticking out downward, a left-second-B projection adapted to be connected to said horizontal bar at the left side of the face and sticking out upward, a right-second-B projection adapted to be connected to said horizontal bar at the right side of the face and sticking out upward, a left-second elastic body connecting said left-second-A projection and said left-second-B projection and biasing said left-second-A projection upward and a right-second elastic body connecting said right-second-A projection and said right-second-B projection and biasing said right-second-A projection upward.

* * * * *